US009833159B2

(12) United States Patent
Chu et al.

(10) Patent No.: US 9,833,159 B2
(45) Date of Patent: Dec. 5, 2017

(54) WEARABLE ELECTRONIC DEVICE

(71) Applicant: ASUSTeK COMPUTER INC., Taipei (TW)

(72) Inventors: Fang-Hsien Chu, Taipei (TW); Chih-Chung Lin, Taipei (TW); Yi-Ting Hsieh, Taipei (TW); Chia-Min Chuang, Taipei (TW); Saou-Wen Su, Taipei (TW); Bin-Chyi Tseng, Taipei (TW); Jian-Sheng Hsieh, Taipei (TW); Tsung-Chieh Yen, Taipei (TW)

(73) Assignee: ASUSTeK COMPUTER INC., Taipei (TW)

( * ) Notice: Subject to any disclaimer, the term of this patent is extended or adjusted under 35 U.S.C. 154(b) by 242 days.

(21) Appl. No.: 14/689,044

(22) Filed: Apr. 16, 2015

(65) Prior Publication Data

US 2016/0062417 A1 Mar. 3, 2016

(30) Foreign Application Priority Data

Aug. 26, 2014 (TW) .............................. 103215235 U

(51) Int. Cl.
*A61B 5/0408* (2006.01)
*G06F 1/16* (2006.01)
*A61B 5/00* (2006.01)

(52) U.S. Cl.
CPC ........ *A61B 5/0408* (2013.01); *A61B 5/04085* (2013.01); *A61B 5/681* (2013.01); *G06F 1/163* (2013.01); *G06F 1/1698* (2013.01)

(58) Field of Classification Search
CPC .......................... A61B 5/0408; A61B 5/04085
See application file for complete search history.

(56) References Cited

U.S. PATENT DOCUMENTS

| | | | | |
|---|---|---|---|---|
| 4,230,127 A | * | 10/1980 | Larson | A61B 5/0404 600/382 |
| 7,171,259 B2 | * | 1/2007 | Rytky | A61B 5/02438 600/509 |
| 8,482,467 B2 | | 7/2013 | Jarvis et al. | |
| 8,508,418 B2 | | 8/2013 | Kough et al. | |
| 9,008,761 B2 | * | 4/2015 | Zdeblick | A61B 5/0408 600/300 |
| 9,281,553 B2 | * | 3/2016 | Tsai | H01Q 1/273 |
| 2010/0112964 A1 | | 5/2010 | Yi et al. | |
| 2014/0266920 A1 | * | 9/2014 | Tran | H01Q 1/243 343/702 |
| 2015/0048979 A1 | * | 2/2015 | Asrani | H01Q 5/0093 343/702 |
| 2015/0091764 A1 | * | 4/2015 | Hsieh | H01Q 5/364 343/702 |

* cited by examiner

*Primary Examiner* — Lee S Cohen
(74) *Attorney, Agent, or Firm* — JCIPRNET

(57) ABSTRACT

A wearable electronic device includes a device body and a wearing element. The wearing element is connected to the device body. The device body includes a conductive upper cover, a conductive lower cover, an insulating frame and a circuit system. The insulating frame is disposed between the conductive upper cover and the conductive lower cover and forms an accommodating space therewith. The circuit system is disposed in the accommodating space. The conductive upper cover has a first feeding point. The conductive lower cover has a second feeding point. The circuit system is coupled to the first feeding point and the second feeding point respectively.

9 Claims, 3 Drawing Sheets

US 9,833,159 B2

WEARABLE ELECTRONIC DEVICE

CROSS-REFERENCE TO RELATED APPLICATION

This application claims the priority benefit of Taiwan application serial no. 103215235, filed on Aug. 26, 2014. The entirety of the above-mentioned patent application is hereby incorporated by reference herein and made a part of this specification.

BACKGROUND OF THE INVENTION

Field of the Invention

The invention relates to an electronic device and, more particularly, to a wearable electronic device.

Description of the Related Art

Conventionally, the size of a wearable electronic device (such as a smart watch) is usually small for wearing. Relatively, the space inside the wearable electronic device for disposing an antenna element is limited. Thus, the antenna element of the conventional wearable electronic device is usually disposed at other space (such as the watchband). However, the bending of the watchband may differ according to the wrist of the user, and the bending would affect the radiating of the antenna element in the watchband. As a result, the wearable electronic device cannot provide a stable wireless transmission function.

BRIEF SUMMARY OF THE INVENTION

A wearable electronic device used for wirelessly communication and to detect electronic signals is provided.

A wearable electronic device includes a device body and a wearing element. The wearing element is connected to the device body. The device body includes a conductive upper cover, a conductive lower cover, an insulating frame and a circuit system. The insulating frame is disposed between the conductive upper cover and the conductive lower cover, and forms an accommodating space therebetween. The circuit system is disposed in the accommodating space. The conductive upper cover includes a first feeding point. The conductive lower cover includes a second feeding point. The circuit system is coupled to the first feeding point and the second feeding point, respectively, and thus the conductive upper cover and the conductive lower cover are regarded as a pair of antenna radiators. The circuit system is coupled to the conductive upper cover and the conductive lower cover, and thus the conductive upper cover and the conductive lower cover are be regarded as a pair of electronic signal detecting electrodes.

These and other features, aspects and advantages of the present invention will become better understood with regard to the following description, appended claims, and accompanying drawings.

DETAILED DESCRIPTION OF THE EMBODIMENTS

Please refer to FIG. 1 to FIG. 4, a wearable electronic device 100 includes a device body 110 and a wearing element 120 is disclosed herein. The wearing element 120 is connected to the device body 110. When the user wears the wearable electronic device 100, the wearing element 120 of the wearable electronic device 100 connects the device body 110 to the user body, such as the wrist. In an embodiment, the wearable electronic device 100 is a watch, where the device body 110 is the body of the watch, and the wearing element 120 is the watchband. In an embodiment, the wearable electronic device 100 is a smart watch, a wristband, a ring or a necklace.

Figure 3:
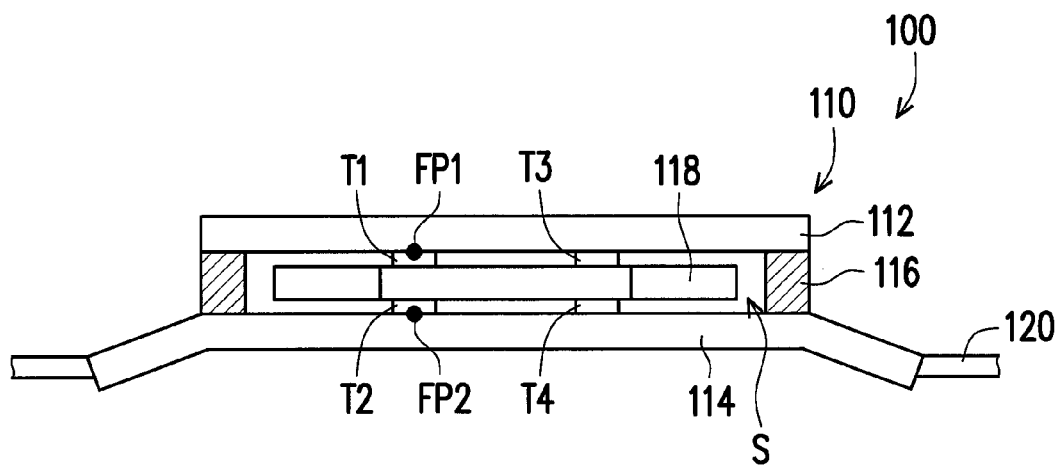
FIG. 3 is a side view showing the wearable electronic device in FIG. 2.

In an embodiment, the device body 110 includes a conductive upper cover 112, a conductive lower cover 114, an insulating frame 116, a circuit system 118 and a display 119. The insulating frame 116 is disposed between the conductive upper cover 112 and the conductive lower cover 114, and the insulating frame 116 forms an accommodating space S between the conductive upper cover 112 and the conductive lower cover 114, as shown in FIG. 3. In an embodiment, the insulating frame 116 is a plastic frame, which is not limited herein. The circuit system 118 is disposed in the accommodating space S, and the circuit system 118 acts like a motherboard. The display 119 is disposed at the conductive upper cover 112 and is coupled to the circuit system 118. The display 119 may include a touch control function.

Figure 1:
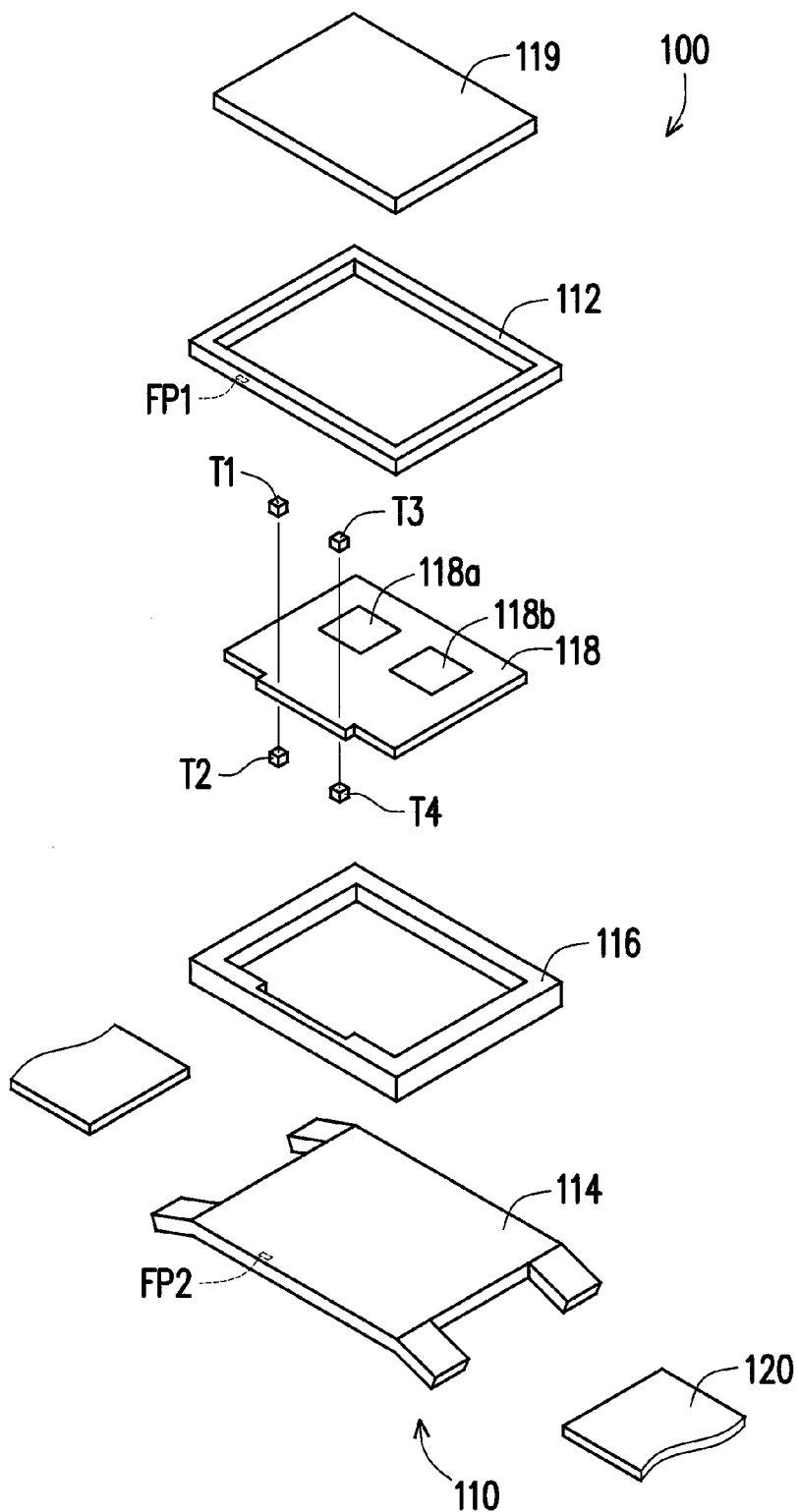
FIG. 1 is an exploded diagram showing a wearable electronic device in an embodiment.
Figure 2:
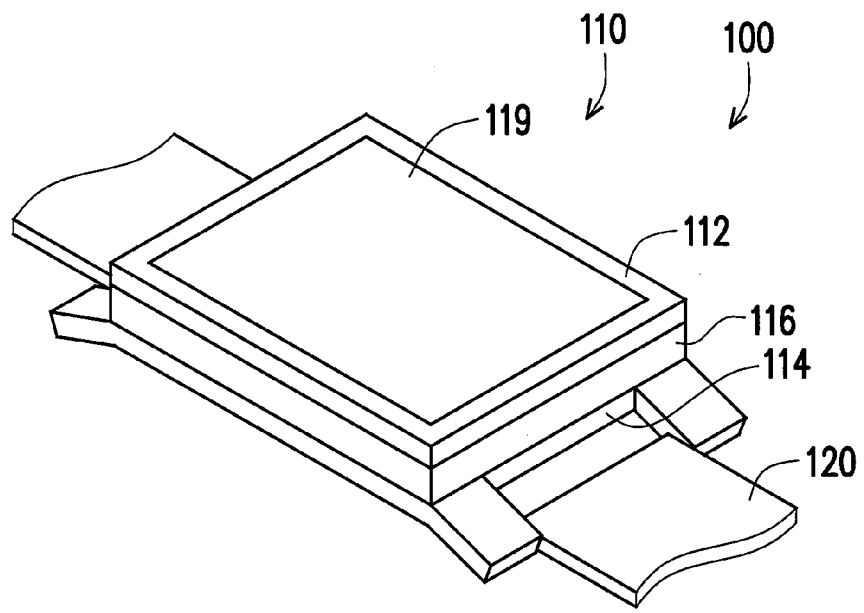
FIG. 2 is a three-dimensional schematic diagram showing the wearable electronic device in FIG. 1.

The conductive upper cover 112 includes a first feeding point FP1, and the conductive lower cover 114 includes a second feeding point FP2, as shown in FIG. 1 and FIG. 3. The circuit system 118 is coupled to the first feeding point FP1 of the conductive upper cover 112 and the second feeding point FP2 of the conductive lower cover. Thus, the conductive upper cover 112 and the conductive lower cover 114 act as antenna radiators, such as a pair of antenna radiators of a dipole antenna, for wireless transmission, such as blue-tooth transmission or wireless local area network (WLAN) transmission. In the embodiment, the distance between the first feeding point FP1 and the second feeding point FP2 is shorter than 7 mm, which is not limited herein.

The circuit system 118 includes a wireless module 118a (such as a blue-tooth chip or a WLAN chip) coupled to the first feeding point FP1 or the second feeding point FP2. In the embodiment, the circuit system 118 includes a first terminal T1 and a second terminal T2. The first terminal T1 and the second terminal T2 are conductive elastic terminals. The wireless module 118a is coupled to the first feeding point FP1 of the conductive upper cover 112 via the first terminal T1. A ground plane G of the circuit system 118 is coupled to the second feeding point FP2 of the conductive lower cover 114 via the second terminal T2. In an embodiment, the conductive upper cover 112 and the conductive lower cover 114 are not only form a part of the outer appearance of the device body 110, but also function as antenna radiators of the wireless module 118a.

Moreover, the conductive upper cover 112 and the conductive lower cover 114 coupled to the circuit system 118 function as a pair of the electronic signal detecting electrodes to detect the physiological signals from the user. In detail, the circuit system 118 includes a physiological sensing module 118b (such as an electrocardiograph (ECG) chip) coupled to the conductive upper cover 112 and the conductive lower cover 114. In the embodiment, the circuit system 118 includes a third terminal T3 and a fourth terminal T4. In an embodiment, the third terminal T3 and the fourth terminal T4 are conductive elastic terminals. The physiological sensing module 118b is coupled to the conductive upper cover 112 via the third terminal T3. The physiological sensing module 118b is connected to the conductive lower cover 114 via the fourth terminal T4. The conductive upper cover 112 and the conductive lower cover 114 are not only form a part of the outer appearance of the device body 110 and act as the antenna radiators, but also function as electronic signal detecting electrodes of the physiological sensing module 118b.

Figure 4:
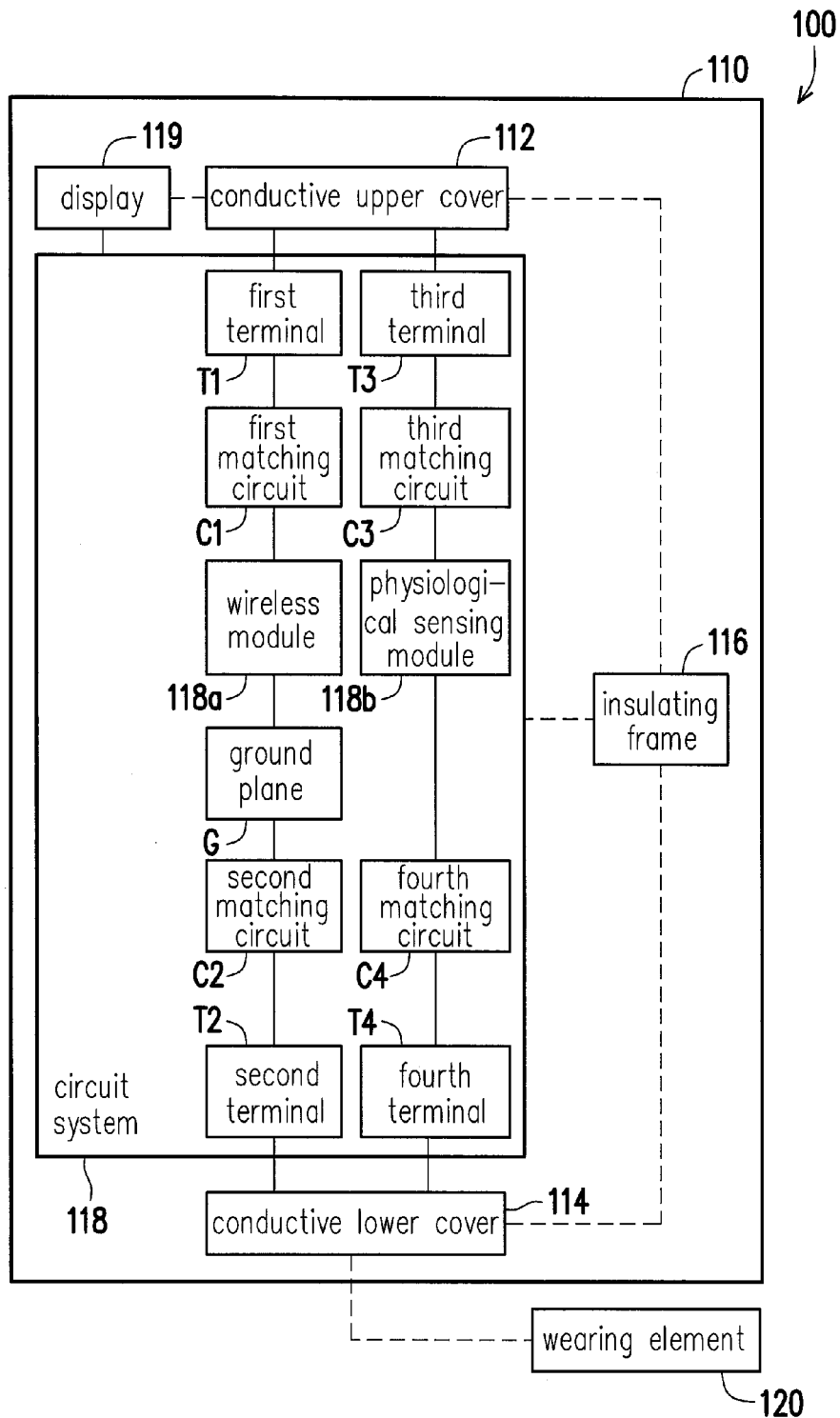
FIG. 4 is a block diagram showing the wearable electronic device in FIG. 1.

As shown in FIG. 4, in the embodiment, the circuit system 118 further includes a first matching circuit C1, a second matching circuit C2, a third matching circuit C3 and a fourth matching circuit C4. The first matching circuit C1 is connected between the wireless module 118a and the first terminal T1 in series. The second matching circuit C2 is connected between the ground plane G of the circuit system 118 and the second terminal T2 in series. The third matching circuit C3 is connected between the physiological sensing module 118b and the third terminal T3. The fourth matching circuit C4 is connected to the physiological sensing module 118b and the fourth terminal T4. The matching circuits C1, C2, C3 and C4 prevent the electronic signal detection and the transmission of the wireless communication signals from being affected.

In detail, when the operating band (which is at a low frequency band) of the ECG signal is detected, the conductive upper cover 112 and the conductive lower cover 114 receives a physiological sensing signal (which is at a low frequency band) via the third matching circuit C3 and the fourth matching circuit C4, and the signals of the wireless module are not affected. When the conductive upper cover 112 and the conductive lower cover 114 act as the antenna radiators (which operate at a high frequency band), the conductive upper cover 112 and the conductive lower cover 114 are conducted by alternating current (AC) via the first matching circuit C1 and the second matching circuit C2, and the signals of the physiological sensing module would not be affected. The matching circuit includes capacitors, inductors and diodes, which is not limited herein.

In sum, the conductive upper cover and the conductive lower cover are not only form a part of the outer appearance of the device body, but also act as a pair of antenna radiators, which saves space occupied by the antenna. At the same time, the conductive upper cover and the conductive lower cover also act as electronic signal detecting electrodes to detect the physiological signals of the body, and thus expense the applications of the wearable electronic device.

Although the present invention has been described in considerable detail with reference to certain preferred embodiments thereof, the disclosure is not for limiting the scope. Persons having ordinary skill in the art may make various modifications and changes without departing from the scope. Therefore, the scope of the appended claims should not be limited to the description of the preferred embodiments described above.

What is claimed is:

1. A wearable electronic device comprising:
  a device body including:
    a conductive upper cover including a first feeding point;
    a conductive lower cover including a second feeding point;
    an insulating frame disposed between the conductive upper cover and the conductive lower cover and forming an accommodating space between the conductive upper cover and the conductive lower cover; and
    a circuit system including a wireless module, disposed in the accommodating space, wherein the wireless module is coupled to the first feeding point and the second feeding point, respectively; and
  a wearing element connected to the device body.

2. The wearable electronic device according to claim 1, wherein a distance between the first feeding point and the second feeding point is shorter than 7 mm.

3. The wearable electronic device according to claim 1, wherein the circuit system includes a first matching circuit, and the wireless module is electrically connected to the first feeding point via the first matching circuit.

4. The wearable electronic device according to claim 1, wherein the circuit system includes a second matching circuit, and a ground plane of the circuit system is electrically connected to the second feeding point via the second matching circuit.

5. The wearable electronic device according to claim 1, wherein the circuit system includes a physiological sensing module, the physiological sensing module is coupled to the conductive upper cover and the conductive lower cover, respectively, and the physiological sensing module senses a physiological signal via the conductive upper cover and the conductive lower cover.

6. The wearable electronic device according to claim 5, wherein the circuit system includes a third matching circuit, and the physiological sensing module is electrically connected to the conductive upper cover via the third matching circuit.

7. The wearable electronic device according to claim 5, wherein the circuit system includes a fourth matching circuit, and the physiological sensing module is electrically connected to the conductive lower cover via the fourth matching circuit.

8. The wearable electronic device according to claim 1, wherein the device body further includes:
  a display disposed at the conductive upper cover and coupled to the circuit system.

9. The wearable electronic device according to claim 1, wherein the insulating frame is a plastic frame.

* * * * *